(12) United States Patent
Hirayama et al.

(10) Patent No.: US 8,497,068 B2
(45) Date of Patent: Jul. 30, 2013

(54) METHOD FOR DETECTING A POSITION OF PROBE ON MICROARRAY

(75) Inventors: Koichi Hirayama, Yamaguchi (JP); Hirofumi Yamano, Yamaguchi (JP); Michifumi Tanga, Yamaguchi (JP)

(73) Assignee: Toyo Kohan Co., Ltd., Tokyo (JP)

( * ) Notice: Subject to any disclaimer, the term of this patent is extended or adjusted under 35 U.S.C. 154(b) by 0 days.

(21) Appl. No.: 13/378,202

(22) PCT Filed: Jun. 10, 2010

(86) PCT No.: PCT/JP2010/060251
§ 371 (c)(1),
(2), (4) Date: Dec. 14, 2011

(87) PCT Pub. No.: WO2010/147167
PCT Pub. Date: Dec. 23, 2010

(65) Prior Publication Data
US 2012/0088690 A1     Apr. 12, 2012

(30) Foreign Application Priority Data

Jun. 16, 2009  (JP) .................................. 2009-143390

(51) Int. Cl.
*C12Q 1/68*     (2006.01)
(52) U.S. Cl.
USPC ....................................................... 435/6.11

(58) Field of Classification Search
USPC ..................................................... 435/6, 287.2
See application file for complete search history.

(56) References Cited

U.S. PATENT DOCUMENTS

| 7,200,254 B2 * | 4/2007 | Kira et al. ..................... 382/129 |
| 2003/0152255 A1 | 8/2003 | Kira et al. |
| 2003/0152256 A1 | 8/2003 | Kira et al. |

FOREIGN PATENT DOCUMENTS

| JP | 2003-307518 | 10/2003 |
| JP | 2009-236626 | 10/2009 |

OTHER PUBLICATIONS

Stears et al, "Trends in microarray analysis," Nature Medicine 2003, 9(1):140-145.*
Hwang, Byeong Hee, et al., "Quantitative Oligonucleotide Microarray Data Analysis With an Artificial Standard Probe Strategy", Biosensors and Bioelectronics, vol. 23, No. 11, (2008), pp. 1738-1744.

* cited by examiner

*Primary Examiner* — Samuel Woolwine
*Assistant Examiner* — Kaijiang Zhang
(74) *Attorney, Agent, or Firm* — McCarter & English

(57) ABSTRACT

A method for detecting hybridization between a probe polynucleotide and a target polynucleotide on a microarray is presented. The method may be used to determine the accuracy of hybridization and possible causes of inaccuracy, such as insufficient washing or deterioration of the microarray.

5 Claims, 8 Drawing Sheets

METHOD FOR DETECTING A POSITION OF PROBE ON MICROARRAY

TECHNICAL FIELD

The present invention relates to a method for detecting hybridization between a probe polynucleotide and a target polynucleotide using a microarray.

This application is a national stage application filed under 35 USC 371 of PCT/JP2010/060251, filed Jun. 10, 2010, which claims the benefit of Japanese Patent Application No. 2009-143390, filed Jun. 16, 2009, both of which are incorporated herein, in their entirety, by reference.

Background of the Invention

Genome-scale elucidation of not only the gene structures of, but also the gene functions of various organisms is underway and the technological development for efficient analyses of gene functions is also rapidly progressing. A microarray is a high-density array wherein many polynucleotides are aligned and immobilized to a carrier such as slide glass within each predetermined region. Microarrays are very useful for determination of the nucleotide sequences of genes, and simultaneous analysis of gene expression, mutation, polymorphism, and the like. The analysis of genetic information using such a microarray is extremely useful for drug discovery research, development of methods for disease diagnosis or disease prevention, and the like.

Detection using a microarray involves firstly hybridization of a target polynucleotide labeled with a radio isotope or a fluorescent dye to a probe polynucleotide aligned at high density on a carrier surface. At this time, the target polynucleotide having a nucleotide sequence complementary to the probe polynucleotide complementarily hybridizes to the probe polynucleotide, and polynucleotides that have not hybridized are removed by washing.

Detection of hybridization using a microarray can result in erroneous determination due to deterioration in performance or insufficient washing thereof, or the like. However, whether or not the relevant determination is erroneous depends on the user of the microarray, resulting in very imprecise judgment. Under such circumstances, treatment of many samples using an automatic apparatus that is a combination of a detector and a reactor has been impossible.

Japanese Patent No. 0880361 discloses a method for determination based on only the results from spots having luminance within a specific range with the use of a microarray on which probe DNAs are spotted in varied concentrations, in order to avoid erroneous determination in a case in which the luminance of a spot is the same as or lower than the minimum limit of detection or is the same as or higher than the maximum limit of detection of a detector. However, with this method, deterioration in performance, insufficient washing of each microarray and the like cannot be detected.

Japanese Patent No. 4261661 discloses a method that involves covalently binding a marker substance to a probe array and then rapidly and precisely specifying the position of a spot of each probe based on the position of the marker substance. However, with such method, deterioration in performance and insufficient washing of each probe array and the like can be detected, but the presence or the absence of hybridization failure cannot be detected, for example.

SUMMARY OF THE INVENTION

An object of the present invention is to provide a means for objectively detecting hybridization failure in addition to deterioration in performance or insufficient washing of each microarray.

The present inventors have discovered that the reliability of each microarray and the reliability of a hybridization reaction can be determined by bringing fluorescence-labeled marker polynucleotides hybridizing to reference polynucleotides and target polynucleotides into contact with microarrays having reference spots at which reference polynucleotides are immobilized, so as to perform a hybridization reaction, and then measuring fluorescence from the reference spots, in addition to detection spots at which the probe polynucleotides are immobilized. Thus, they have completed the present invention.

The present invention encompasses the following (1) to (7).

(1) A method for detecting hybridization between a probe polynucleotide and a target polynucleotide using a microarray, comprising the steps of:
  1) bringing a fluorescence-labeled target polynucleotide and a fluorescence-labeled marker polynucleotide hybridizing to a reference polynucleotide into contact with a microarray having reference spots at one or more positions at which the reference polynucleotide is immobilized, in addition to a plurality of detection spots at which the probe polynucleotide is immobilized;
  2) washing the microarray to remove unreacted target polynucleotides;
  3) measuring fluorescence at the reference spot(s) and determining that measurement is possible if the measured value meets a predetermined level; and
  4) measuring fluorescence at each detection spot at which the probe polynucleotide is immobilized if measurement is determined to be possible.
(2) The method according to (1), wherein the fluorescent label of the marker polynucleotide is identical to that of the target polynucleotide.
(3) The method according to (1) or (2), wherein in the microarray, the detection spots and the reference spots are aligned and arranged, the reference spots are present at at least two positions, and the position of a detection spot is detected based on the distances from the reference spots and angles from a reference line, where the reference line is a line connecting the reference spots at any two positions.
(4) The method according to (3), wherein the detection spots and the reference spots are arranged in a lattice pattern so that the circumference thereof is quadrangular and the reference spots are present at different vertices of a quadrangle.
(5) The method according to (1) or (2), wherein in the microarray, the detection spots and the reference spots are aligned and arranged in a lattice pattern so that the circumference thereof is square or rectangular, the reference spots are present at two positions located at vertices on the diagonal line thereof, an intersection point, where two lines that run through each reference spot vertically cross, is detected, the lengths of two connections that connect the intersection point to each reference spot are detected, and the position of each detection spot located on the connections is detected based on the lengths of the connections and the number of spots.
(6) The method according to any one of (1) to (5), wherein the marker polynucleotide has 95% or more homology with a polynucleotide complementary to the reference polynucleotide.
(7) A kit for detecting hybridization between a probe polynucleotide and a target polynucleotide comprising a microarray having reference spots at one or more positions, at which reference polynucleotides are immobilized, in addition to a plurality of detection spots at which a probe polynucleotide is immobilized, and a fluorescence-labeled marker polynucleotide hybridizing to the reference polynucleotide.

This description includes part or all of the contents as disclosed in the description and/or drawings of Japanese Patent Application No. 2009-143390, which is a priority document of the present application.

DETAILED DESCRIPTION OF THE INVENTION

Figure 1:
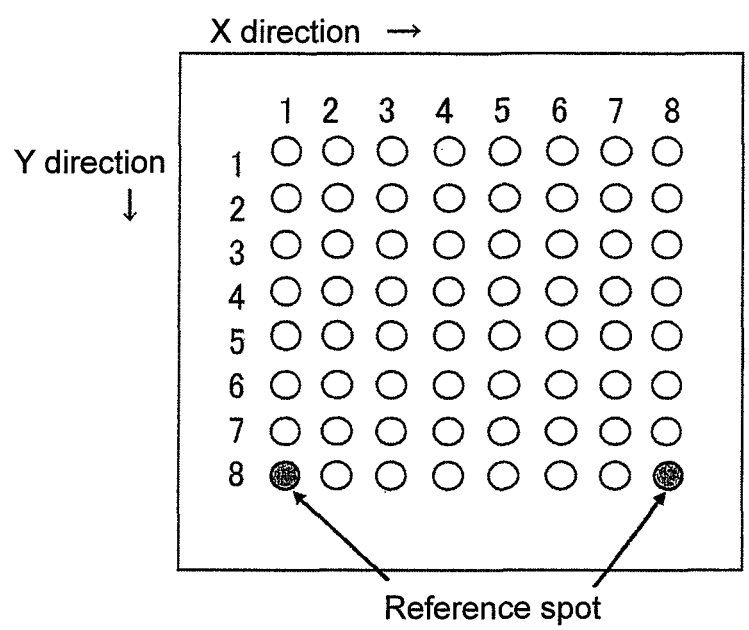
FIG. 1 shows an embodiment of arrangement of probe DNA spots and reference DNA spots in a microarray.

The present invention relates to a method for detecting hybridization between probe polynucleotides and target polynucleotides using a microarray.

In the present invention, examples of polynucleotides include oligonucleotides and nucleic acids including DNA and RNA. Examples of DNA include single-stranded DNA and double-stranded DNA. Also, examples of nucleic acids include an artificial nucleic acid with a modified diester phosphate site; an artificial nucleic acid with a modified glycosyl linkage or hydroxyl group at a furanose site; an artificial nucleic acid with a modified nucleic acid base site; and an artificial nucleic acid utilizing a structure other than the sugar-phosphate backbone. More specific examples thereof include a phosphorothioate-type artificial nucleic acid, a phosphorodithioate-type artificial nucleic acid, a phosphorodiamidate-type artificial nucleic acid, and a methylphosphonate-type or methylphosphonothioate-type artificial nucleic acid, in which an oxygen atom at a phosphoric acid site is substituted with a sulfur atom; a substituent (on a furanose ring)-modified type artificial nucleic acid, a pyranose-type artificial nucleic acid having the sugar ring backbone to which one carbon is added, or a polycyclic sugar backbone-type artificial nucleic acid; and a pyrimidine C-5-modified base-type artificial nucleic acid, a purine C-7-modified base-type artificial nucleic acid, or a ring-expanded (-modified) base-type artificial nucleic acid.

In the present invention, the term "probe polynucleotide(s)" has a meaning generally used in the art and refers to a polynucleotide(s) that is used for detecting a target gene, a polynucleotide(s) corresponding to a target gene, or a polynucleotide(s) specifically hybridizing to a fragment thereof. As a probe polynucleotide(s), in general, a synthetic oligonucleotide, cDNA and genomic DNA, a fragment(s) thereof, and modified products thereof (e.g., a single-stranded probe polynucleotide is altered to a double-stranded probe polynucleotide) are used, for example. A probe polynucleotide generally has 3 to 5000 nucleotides and preferably has 10 to 1000 nucleotides. The concentration of a spotting solution of probe polynucleotides to be immobilized in a microarray generally ranges from 1 µM to 10 µM.

In the present invention, the term "target polynucleotide(s)" has a meaning generally used in the art and refers to a polynucleotide(s) to be subjected to detection. A "target polynucleotide" may also be referred to as a "polynucleotide of interest". In general, a test sample-derived polynucleotide or a polynucleotide enzymatically synthesized/amplified based on the aforementioned polynucleotide, and specifically, mRNA, cDNA, aRNA, fragments thereof, and modified products thereof are used, for example.

The term "hybridize," "hybridization reaction," or "hybridization" has a meaning generally used in the art and refers to the formation of double stranded polynucleotides having sequences complementary to each other, such as single-stranded DNAs, single-stranded RNAs, or single-stranded DNA and single-stranded RNA under appropriate conditions. In the present invention, hybridization is performed preferably under stringent conditions.

In the present invention, fluorescence-labeled target polynucleotides are used. Types of labeling method or label are not particularly limited, as long as they enable detection of hybridization between probe polynucleotides and target polynucleotides, and are known in the art. For example, a target polynucleotide is synthesized or amplified so as to incorporate a substrate (mainly, UTP) to which a fluorescent label is covalently bound, so that a fluorescence-labeled target polynucleotide can be obtained. Examples of a fluorescent label include CyDye such as Cy3 and Cy5, FITC, RITC, rhodamine, Texas Red, TET, TAMRA, FAM, HEX, and ROX.

In the present invention, as a microarray, a microarray having reference spots at which reference polynucleotides are immobilized at one or more, preferably at least two, more preferably 2 to 4, and further preferably 2 positions, in addition to a plurality of detection spots at which probe polynucleotides are immobilized, is used. A reference polynucleotide generally has 3 to 5000 nucleoteides and preferably 10 to 1000 nucleotides. The concentration of a spotting solution of reference polynucleotides to be immobilized in reference spots generally ranges from 1 µM to 10 µM.

In the present invention, a hybridization reaction is performed by bringing fluorescence-labeled target polynucleotides and fluorescence-labeled marker polynucleotides hybridizing to reference polynucleotides into contact with the above microarray. After removal of unreacted target polynucleotides by washing, firstly fluorescence at reference spots is measured. The term "a fluorescence-labeled marker polynucleotide(s) hybridizing to a reference polynucleotide(s)" generally refers to a fluorescence-labeled marker polynucleotide(s) hybridizing under stringent conditions to a reference polynucleotide(s).

The term "stringent conditions" refers to conditions in which specific hybrids are formed, but non-specific hybrids are not formed. Examples of such conditions include low stringent conditions and high stringent conditions. High stringent conditions are preferable. The term "low stringent conditions" refers to conditions in which post-hybridization washing is performed at 42° C. in 5×SSC and 0.1% SDS, preferably at 50° C. in 5×SSC and 0.1% SDS, for example. The term "high stringent conditions" refers to conditions in which post-hybridization washing is performed at 65° C. in 0.1×SSC and 0.1% SDS, for example. Under the stringent conditions described above, a polynucleotide comprising a nucleotide sequence having high homology (80% or more, preferably 90% or more, more preferably 95% or more, even more preferably 98% or more homology) with a polynucleotide complementary to a reference polynucleotide can hybridize to the reference polynucleotide.

As described above, a marker polynucleotide is designed to hybridize to a reference polynucleotide and has a fluorescent label. Hence, fluorescence must be detected from reference spots unless a target polynucleotide hybridizes to a probe. No detection of fluorescence or a low fluorescence level indicates that the reference polynucleotide has disappeared from the microarray; that is, other probe polynucleotides have similarly disappeared. Alternatively, the same may indicate hybridization reaction failure. Therefore, fluorescence at reference spots is measured and then whether or not a predetermined level is satisfied is determined, so that whether or not the microarray has experienced deterioration can be determined. In other words, the reliability of the microarray can be determined. Furthermore, the reliability of a hybridization reaction can be determined.

Fluorescent labels for marker polynucleotides are not particularly limited, but fluorescent labels that are the same as those for target polynucleotides are preferably used. Through the use of the same fluorescent labels, the fluorescent labels of the marker polynucleotides and the target polynucleotides can be collectively detected using the same detector, enabling rapid and convenient measurement.

In a microarray to be used in the present invention, preferably, spots (detection spots) for probe polynucleotides and reference spots are aligned and preferably arranged in a lattice pattern. Preferably, the reference spots are present at at least two positions. The position of each detection spot (specifically, the center of each detection spot) is detected based on the distances from the reference spots and angles from a reference line, where the reference line is a line connecting the reference spots at any two positions. More specifically, the central position of each spot can be determined based on the distances from reference spots, angles from the reference line (i.e. angles between a line connecting each detection spot and a reference spot and the reference line, spot pitch, and the like, if necessary.

Also, detection spots and reference spots are aligned and arranged in a lattice pattern, so that the circumference thereof is square or rectangular and the reference spots can be present at two different vertices facing each other on a diagonal line. In this case, an intersection point, at which two lines that pass through these reference spots and cross vertically, is detected, and two connections that connect the intersection point to reference spots at two positions are detected. Subsequently, the length of each connection is calculated and then the distance thereof is divided by predetermined number (=the number of spots on the circumference of the quadrangle−1), so that each spot interval on the connection can be found. Thus, each spot position can be detected based on the spot interval. For example, suppose that a microarray with 4 lines of spots×4 columns of spots is used. In this case, the number of spots along a connection is 4. If the length of the connection is 900 µm the spot interval can be found by 900/(4−1)=300. Thus, the spot interval in this case is 300 µm. With the formula, a position that is at a distance of 300 µM from a reference spot along the connection can be determined to be the center of the spot. Furthermore, a position that is at a distance of 300 µm from the center along the connection can be determined to be the center of the next spot.

Reference spots at two positions forming the reference line are preferably present at remote positions from each other among a group of spots aligned on a microarray. Preferably, detection spots and reference spots are arranged in a lattice pattern so that the circumference thereof is quadrangular (e.g., FIG. 1), and the reference spots are present at different vertices of the quadrangle.

As a detector for measuring fluorescence at detection spots and reference spots, a fluorescence laser microscope, a cooled CCD camera, or a fluorescence scanning apparatus to which a computer is connected is used, for example. Thus, fluorescence intensity on the microarray can be automatically measured. Confocal or non-focal laser may be used instead of a CCD camera. Thus, image data can be obtained. From the thus obtained data, target polynucleotides complementary to probe polynucleotides immobilized on a microarray can be identified. This makes it possible to create gene expression profiles based on the results or to determine the nucleotide sequence of the polynucleotide.

The microarray to be used in the present invention is prepared by immobilizing probe polynucleotides and reference polynucleotides on a carrier. As materials for carriers, materials known in the art can be used and are not particularly limited. Examples of such materials include: noble metals such as platinum, platinum black, gold, palladium, rhodium, silver, mercury, tungsten, and compounds thereof; conductive materials such as graphite and carbon represented by carbon fiber; silicon materials represented by single crystal silicon, amorphous silicon, silicon carbide, silicon oxide, silicon nitride, and composite materials of such silicon materials, represented by SOI (silicon×on×insulator) and the like; inorganic materials such as glass, quartz glass, alumina, sapphire, ceramics, forsterite, and photosensitive glass; and organic materials such as polyethylene, ethylene, polypropylene, cyclic polyolefin, polyisobutylene, polyethylene terephthalate, unsaturated polyester, fluorine-containing polymer, polyvinyl chloride, polyvinylidene chloride, polyacetic acid vinyl, polyvinyl alcohol, polyvinyl acetal, acrylresin, polyacrylonitrile, polystyrene, acetal resin, polycarbonate, polyamide, phenol resin, urea resin, epoxy resin, melamine resin, styrene-acrylonitrile copolymer, acrylonitrile-butadienestyrene copolymer, polyphenylene oxide, and polysulfone. The shape of such a carrier is not particularly limited, and has preferably a planar shape.

Preferably, a carrier having a carbon layer and a chemical modification group on the surface is used. Examples of such a carrier having a carbon layer and a chemical modification group on the surface include a carrier having a carbon layer and a chemical modification group on the substrate surface and a carrier having a chemical modification group on the surface of a substrate comprising a carbon layer. As materials for a substrate, materials known in the art can be used and are not particularly limited. Materials similar to those listed as materials for a carrier can be used.

A carrier having a fine planar structure is preferably used herein. The shape of such a carrier is not limited, such as a rectangular shape, a square shape, and a circular shape. In general, a carrier that is used herein is generally 1 mm to 75 mm square, preferably 1 mm to 10 mm square, and more preferably 3 mm to 5 mm square. A substrate made of a silicon material or a resin material is preferably used, since a carrier having a fine planar structure can be easily produced. In particular, a carrier having a carbon layer and a chemical modification group on the surface of a substrate comprising single crystal silicon is preferably used. Examples of such single crystal silicon include single crystal silicon in which the orientation of the crystallographic axis is slightly and partially varied (which may also be referred to as "mosaic crystal") and single crystal silicon containing atomic scale disorders (lattice defects).

Examples of carbon layers that are preferably used or formed on a substrate include, but are not particularly limited to, surfaces of synthetic diamond, high pressure synthetic diamond, natural diamond, soft diamond (e.g., diamond-like carbon), amorphous carbon, or carbonaceous matter (e.g., graphite, fullerene, and carbon nanotubes), mixtures thereof, or laminated products thereof. Also, carbides such as a hafnium carbide, a niobium carbide, a silicon carbide, a tantalum carbide, a thorium carbide, a titanium carbide, a uranium carbide, a tungsten carbide, a zirconium carbide, a molybdenum carbide, a chrome carbide, and a vanadium carbide can also be used. Here the term "soft diamond" is a generic name used for incomplete diamond structures that are mixtures of diamond and carbon, such as namely Diamond Like Carbon (DLC), and the mixture fractions thereof are not particularly limited.

A carbon layer can be formed by a known method. Examples of such method include a microwave plasma CVD (chemical vapor deposit) method, an ECRCVD (electric cyclotron resonance chemical vapor deposit) method, an ICP (inductive coupled plasma) method, a direct current sputtering method, an ECR (electric cyclotron resonance) sputtering method, an ionized evaporation method, an arc evaporation method, a laser evaporation method, an EB (electron beam) evaporation method, and a resistance heating evaporation method.

When a carbon layer is formed on the surface of a substrate, the thickness of the carbon layer is generally up to about 100 µm in terms of the monomolecular layer. Excessive thinness thereof may result in the surface of a foundation substrate being locally exposed, but excessive thickness thereof results in poor productivity. Hence, the thickness preferably ranges from 2 nm to 1 µm and more preferably ranges from 5 nm to 500 nm.

Through introduction of a chemical modification group onto the surface of a substrate with a carbon layer formed thereon, oligonucleotide probes can be firmly immobilized on the carrier. A chemical modification group to be introduced can be appropriately selected by persons skilled in the art and is not particularly limited. Examples thereof include an amino group, a carboxyl group, an epoxy group, a formyl group, a hydroxyl group, and an active ester group.

An amino group can be introduced by subjecting a carbon layer to ultraviolet (UV) irradiation in an ammonia gas or to plasma treatment, for example. Alternatively, an amino group can be introduced by subjecting a carbon layer to UV irradiation in a chlorine gas for chlorination and then further subjecting the same to UV irradiation in an ammonia gas. Alternatively, an amino group can also be introduced by performing a reaction with a chlorinated carbon layer in a polyvalent amine gas such as methylene diamine or ethylene diamine.

A carboxyl group can be introduced by reacting an appropriate compound with the above-aminated carbon layer, for example. Examples of a compound to be used for introduction of a carboxyl group include: halo carboxylic acid represented by the formula: $X-R^1-COOH$ (wherein X denotes a halogen atom and $R^1$ denotes a C10-12 divalent hydrocarbon group), such as chloroacetic acid, fluoroacetic acid, bromoacetic acid, iodoacetic acid, 2-chloropropionic acid, 3-chloropropionic acid, 3-chloroacrylic acid, and 4-chlorobenzoic acid; dicarboxylic acid represented by the formula: $HOOC-R2-COOH$ (wherein $R^2$ denotes a single bond or C1-12 divalent hydrocarbon group), such as oxalic acid, malonic acid, succinic acid, maleic acid, fumaric acid, and phthalic acid; polyvalent carboxylic acid such as polyacrylic acid, polymethacrylic acid, trimellitic acid, and butane tetracarboxylic acid; keto acid or aldehyde acid represented by the formula: $R^3-CO-R^4-COOH$ (wherein $R^3$ denotes a hydrogen atom or C1-12 divalent hydrocarbon group and $R^4$ denotes a C1-12 divalent hydrocarbon group); monohalides of dicarboxylic acid represented by the formula: $X-OC-R^5-COOH$ (wherein X denotes a halogen atom and $R^5$ denotes a single bond or C1-12 divalent hydrocarbon group), such as succinic acid monochloride and malonic acid monochloride; and acid anhydrides such as anhydrous phthalic acid, anhydrous succinic acid, anhydrous oxalic acid, anhydrous maleic acid, and anhydrous butane tetracarboxylic acid.

An epoxy group can be introduced by reacting an appropriate polyvalent epoxy compound with the above aminated carbon layer, for example. Alternatively, an epoxy group can be introduced by reacting organic peracid with a carbon=carbon double bond contained in a carbon layer. Examples of organic peracid include peracetic acid, perbenzoic acid, diperoxyphthalic acid, performic acid, and trifluoro peracetic acid.

A formyl group can be introduced by reacting glutaraldehyde with the above-aminated carbon layer, for example.

A hydroxyl group can be introduced by reacting water with the above-chlorinated carbon layer, for example.

The term "active ester group" refers to an ester group having an electron-withdrawing group with high acidity on the alcohol side of an ester group and activating nucleophilic reaction. Such active ester group specifically refers to an ester group with high reaction activity. An active ester group has an electron-withdrawing group on the alcohol side of the ester group, which is activated to a degree higher than alkyl ester. Such active ester group has reactivity to a group such as an amino group, a thiol group, and a hydroxyl group. More specifically, phenol esters, thiophenol esters, N-hydroxyamine esters, cyanomethyl esters, esters of heterocyclic hydroxy compounds, and the like are known as active ester groups having activity much higher than that of alkyl esters and the like. More specifically, examples of such active ester group include a p-nitro phenyl group, an N-hydroxysuccinimide group, a succinimide group, a phthalic imide group, and a 5-norbornene-2,3-dicarboxyimide group. In particular, an N-hydroxysuccinimide group is preferably used.

An active ester group can be introduced by performing active-esterification of the above-introduced carboxyl group using a dehydrating and condensing agent such as cyanamide and carbodiimide (e.g., 1[3-(dimethylamino)propyl]-3-ethyl carbodiimide) and a compound such as N-hydroxysuccinimide. As a result of this treatment, a group can be formed wherein an active ester group such as an N-hydroxysuccinimide group binds to an end of a hydrocarbon group via amide bond (JP Patent Publication (Kokai) No. 2001-139532).

Probe polynucleotides and reference polynucleotides are each dissolved in a spotting buffer, so as to prepare spotting solutions. The solutions are dispensed into 96-well or 384-well plastic plates. The dispensed solutions are spotted onto carriers using a spotter (apparatus) or the like, so that a microarray can be produced. Alternatively, spotting solutions may be spotted manually using a micropipetter.

After spotting, incubation is preferably performed to proceed a reaction of binding probe polynucleotides and reference polynucleotides to a carrier. Incubation is generally performed at temperatures ranging from −20° C. to 100° C. and preferably ranging from 0° C. to 90° C. for generally 0.5 to 16 hours and preferably for 1 to 2 hours. Incubation is desirably performed in a high-moisture atmosphere under conditions of humidity ranging from 50% to 90%, for example. Subsequent to incubation, the resultant is preferably washed using a wash (e.g., 50 mM TBS/0.05% Tween 20, 2×SSC/0.2% SDS solution, and ultrapure water), in order to remove DNA not binding to the carrier.

In an embodiment of the present invention, the following steps are preferably performed after the step of removing target polynucleotides that have remained unreacted by washing the microarray and before actual measurement (that is, measurement of fluorescence at each detection spot in which probe polynucleotides have been immobilized). The following steps may be performed before or after measurement of fluorescence at reference spots.

The steps are as follows: a step of measuring luminance at a position having a specified distance away from the center of each spot of a plurality of spots to obtain a plurality of background values; a step of calculating a representative background value representing the thus obtained plurality of background values; and a step of calculating a difference between the background value and representative background value for all spots or all spots for which background values have been measured, and then determining that measurement is impossible if spots having a difference that is the same as or higher than a predetermined value are present.

Spots as mentioned herein include both detection spots and reference spots. Regarding a plurality of spots for which background values are obtained, it is preferable to measure background values for all spots that form at least the circumference from among spots that are aligned and arranged in a microarray. Also, measurement of background values is not required for all spots, but background values of all spots may be measured. A plurality of spots for which background values are measured are, when detection spots and reference spots are arranged in a lattice pattern so that the circumference is quadrangular, for example, generally at least 2 spots at vertices of a quadrangle, preferably at least 4 spots at vertices of a quadrangle, and more preferably all spots on the circumference. More specifically, such "plurality of spots" corresponds to 60 spots on the circumference in the case of 16 lines of spots×16 columns of spots or all 256 spots in the case of 16 lines of spots×16 columns of spots.

Figure 8:
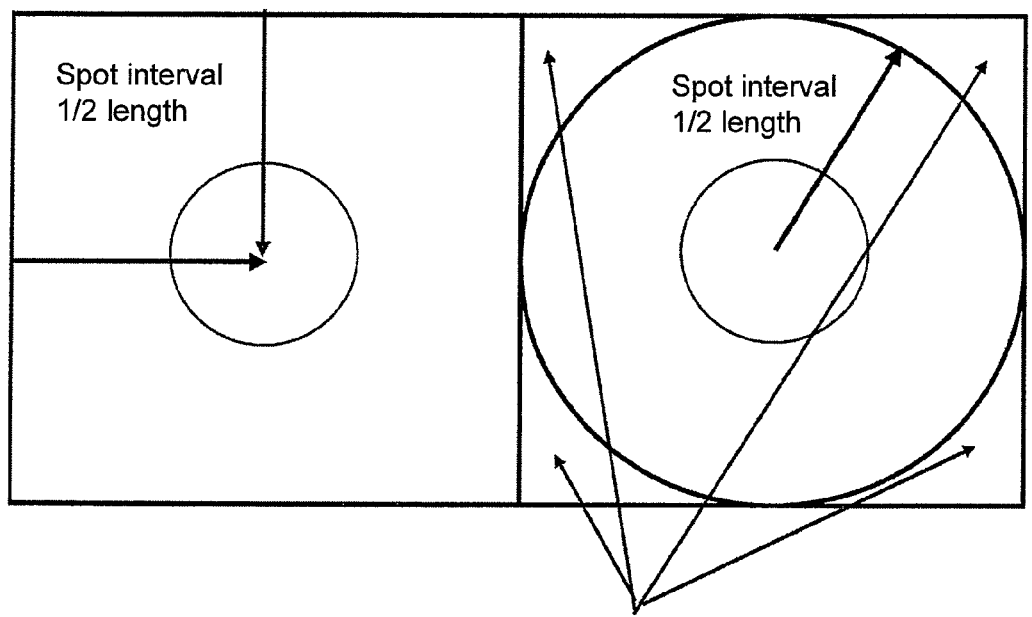
FIG. 8 shows positions within a specified range from the center of a spot for measurement of luminance as a background value calculation example.

When luminance at a position having a specified distance away from the center of each spot is measured to obtain each background value, a specified (distance) range from the center of each spot is appropriately determined based on the size of the spot, spot interval, and the like. For example, as shown in FIG. 8, a specified (distance) range can be within a quadrangle range having a spot interval (length) as a side that is the same as or longer than the specified distance from the center of the relevant spot, wherein the center of the quadrangle is the central position of the spot. For example, a specified (distance) range is within the range of a rectangle having a side of 1000 μm when the distance from the center of a spot to a side of the quadrangle is 70 μm or more and preferably a specified (distance) range is within the range of a rectangle having a side of 380 μm when the distance from the center of a spot to a side of the quadrangle is 70 μm or more. Also, a mean value of luminance values measured for all or some of spots at positions within a specified range may be regarded as a background value. Alternatively, luminance of only one spot at a position within a specified range is measured and the result may be regarded as a background value.

Methods for positioning the center of a spot are not particularly limited. For example, a portion having predetermined fluorescence intensity (e.g., 3000 or more) in each spot is detected and the portion can be determined to be the center thereof. Alternatively, a line that connects the centers of the reference spots at 2 positions is determined to be a reference line. Then the central position of each detection spot may be determined based on the distances from reference spots, angles from a reference line, and a spot pitch, for example.

A representative background value is not particularly limited, as long as it represents a plurality of background values measured, and is preferably a mean value or a median value of a plurality of background values.

The difference between the background value and the representative background value is calculated for all spots or all spots for which background values are measured. When a spot exhibiting a difference that is the same as or higher than a predetermined value is present, it can be determined that background values of the area surrounding the spot vary significantly. Therefore, it can be determined that measurement is impossible with the microarray because of insufficient washing or a lack of reliability. Here, the predetermined value differs depending on conditions and the like. For example, when an image is displayed with 16 bit pitch, the value can be determined to be 1000 or more. When an image is displayed with 8 bit pitch, for example, the value can be determined to be less than 50.

In another embodiment of the present invention, the following steps are preferably performed after the step of removing target polynucleotides that have remained unreacted by washing the microarray and before actual measurement (that is, measurement of fluorescence at each detection spot in which probe polynucleotides are immobilized). The following steps may be performed before or after measurement of fluorescence at reference spots.

The steps are as follows: a step of measuring luminance at a position having a specified distance away from the center of each spot of plurality of spots to obtain a plurality of background values; a step of calculating a mean value or a median value of a plurality of background values as a representative background value; and a step of determining that measurement is impossible if the representative background value is the same as or higher than a predetermined value.

Here, spots as mentioned herein include both detection spots and reference spots. Regarding a plurality of spots for which background values are obtained, it is preferable to measure background values for all spots that form at least the circumference from among spots that are aligned and arranged in a microarray. Also, measurement of background values is not required for all spots, but background values of all spots may be measured. A plurality of spots for which background values are measured are, when detection spots and reference spots are arranged in a lattice pattern so that the circumference is quadrangular, for example, generally at least 2 spots at vertices of a quadrangle, preferably at least 4 spots at vertices of a quadrangle, and more preferably all spots on the circumference. More specifically, such "plurality of spots" corresponds to 60 spots on the circumference in the case of 16 lines of spots×16 columns of spots or all 256 spots in the case of 16 lines of spots×16 columns of spots.

A method for determining a specified distance from the center of a spot and the center is as described above.

When a representative background value that is a mean value or a median value of a plurality of background values is the same as or higher than a predetermined value, background values of an area surrounding the relevant spot are generally high. Therefore, it can be determined that measurement is impossible with the microarray because of insufficient washing or a lack of reliability. Such a predetermined value differs depending on conditions and the like. For example, in the case of 16 bit, a predetermined value can be determined to be 1000 or more.

The present invention also relates to a kit for use in detection of hybridization between the above probe polynucleotides and target polynucleotides. The kit of the present invention comprises, a microarray having a reference spot(s) in which reference polynucleotides are immobilized at one or more positions, in addition to a plurality of detection spots at which probe polynucleotides are immobilized, and fluorescence-labeled marker polynucleotides hybridizing to the reference polynucleotides. Such probe polynucleotides, target polynucleotides, reference polynucleotides, a microarray, marker polynucleotides, and the like are as described above. The kit of the present invention may further comprise a hybridization buffer, a washing buffer, microplates, nylon membranes, and the like.

Hereafter, the present invention is described in greater detail with reference to the examples, although the technical scope of the present invention is not limited thereto.

EXAMPLES

Example 1

Preparation of a Carrier

Film formation of two DLC layers was performed on a silicon substrate (3 mm on each side) using an ionized evaporation method under the following conditions.

TABLE 1

| | | 1st layer | 2nd layer | |
|---|---|---|---|---|
| Raw material gas | CH$_4$ | 4.75 | 47.5 | (sscm) |
| | H$_2$ | 0.25 | 2.5 | (sscm) |
| Working pressure | | 3.0 | 8.0 | (Pa) |
| Substrate bias | Direct-current voltage | 500 | 500 | (V) |
| | High-frequency output | 100 | — | (W) |
| Anode voltage | | 50 | 50 | (V) |
| Filament | Voltage | 7 | 7 | (V) |
| | Current | 22 | 22 | (A) |

An amino group was introduced onto the thus obtained silicon substrate having DLC layers on its surface using ammonia plasma under the following conditions.

TABLE 2

| Raw material gas | NH$_3$ | 30 | (sscm) |
|---|---|---|---|
| Working pressure | | 8.0 | (sscm) |
| Substrate bias | Direct-current voltage | 500 | (Pa) |
| | High-frequency output | — | (W) |
| Anode voltage | | 50 | (V) |
| Filament | Voltage | 7 | (V) |
| | Current | 22 | (A) |

A carboxyl group was introduced with 30 minutes of immersion in a 1-methyl-2-pyrrolidone solution containing 140 mM succinic anhydride and 0.1 M sodium borate. Activation was performed with 30 minutes of immersion in a solution containing a 0.1 M potassium phosphate buffer, 0.1 M 1[3-(dimethylamino)propyl]-3-ethyl carbodiimide, and 20 mM N-hydroxysuccinimide. Thus, a carrier having DLC layers on the surface of a silicon substrate and a N-hydroxysuccinimide group as a chemical modification group was obtained.

Example 2

Preparation of a Microarray

Reference DNA (reference polynucleotide) and probe DNA (probe polynucleotide) were each dissolved in Sol. 6 and then the resultant was spotted on the carrier prepared in Example 1 so that the spots were arranged as shown in FIG. 1 (Hitach, Ltd. Software, SPBIO). Specifically, the reference DNA was spotted at reference spots and the probe DNA was spotted at detection spots. In FIG. 1, spots other than spots indicated as reference spots are detection spots. In addition, the probe DNA was spotted with different concentrations. The spot pitch employed herein was 280 μm. The sequences of the reference DNA and the probe DNA are as follows.

```
Reference DNA:
5'-ACTGGCCGTCGTTTTACAACGT-3'        (SEQ ID NO: 1)

Probe DNA:
5'-TTGTCCGCGCCGGGCTTCGCTC-3'        (SEQ ID NO: 2)
```

After 1 hour of baking at 80° C., washing was performed for 15 minutes in 2×SSC/0.2% SDS at room temperature during agitation, so that a microarray in which the probe DNA and the reference DNA had been spotted was prepared.

Example 3

Hybridization to Target DNA (1) Regions hybridizing to the probe DNA were amplified by PCR using the lambda phage genomic DNA as a template and the following primer set.

```
Primer 1: 5'-ACAGGGAATGCCCGTTCTGC-3' (SEQ ID NO: 3)

Primer 2: 5'-AATAACCGACACGGGCAGAC-3' (SEQ ID NO: 4)
```

Labeling was performed using CyDye (Cy5). The composition of the PCR solution is as follows.

TABLE 3

| Primer 1 (10 μM) | 1 μL |
|---|---|
| Primer 2 (10 μM) | 1 μL |
| PCR Buffer | 2 μL |
| dNTP (the concentration of dCTP was 1/10 that of dNTP) | 2 μL |
| Cy5-dCTP | 0.5 μL |
| Template DNA | 1 μL |
| Ex Tap | 0.1 μL |
| H$_2$O | 13 μL |
| total | 20.6 μL |

(2) Oligo DNA (marker polynucleotide) fluorescence-labeled with Cy5 was added to a hybridization buffer (3×SSC/0.3% SDS). The oligo DNA was a complementary strand of the reference DNA.

```
Oligo DNA:
5'-ACGTTGTAAAACGACGGCCAGT-3'        (SEQ ID NO: 5)
```

(3) One μL of the hybridization buffer supplemented with the fluorescence-labeled oligo DNA and 2 μL of the PCR product obtained in (1) were mixed. The mixture was added dropwise to the microarray prepared in Example 2, and then hybridization was performed at 55° C. for 1 hour, followed by washing with 2×SSC/0.2% SDS and then with 2×SSC.

Figure 2:
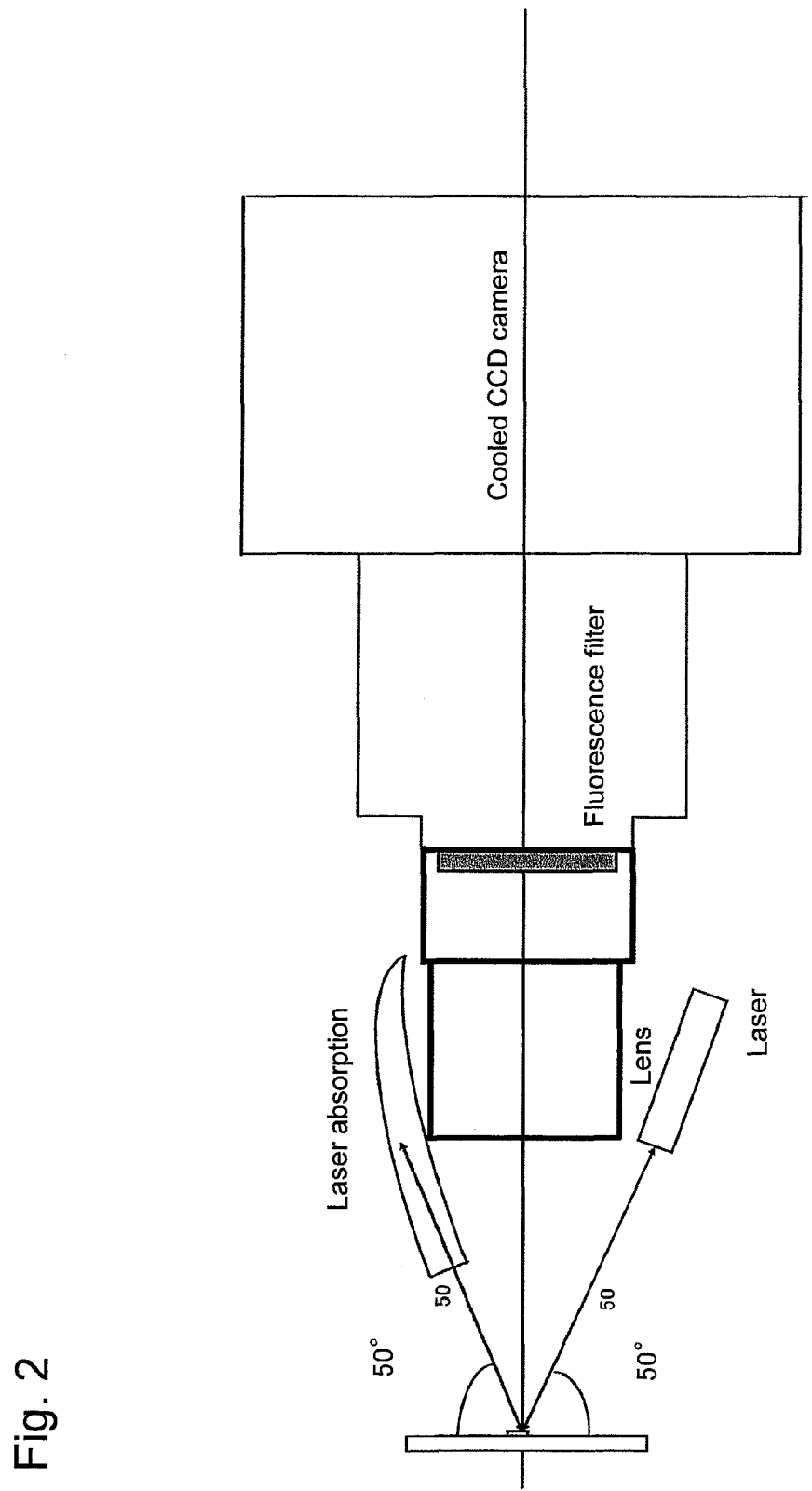
FIG. 2 shows an embodiment of a detector to be used for fluorescence detection using a microarray.

(4) Fluorescence was measured using a detector as shown in FIG. 2. The entire surface of the microarray was irradiated with excitation light using a laser. Light having a wavelength other than the target wavelength was cut using a fluorescent filter.

Figure 3:
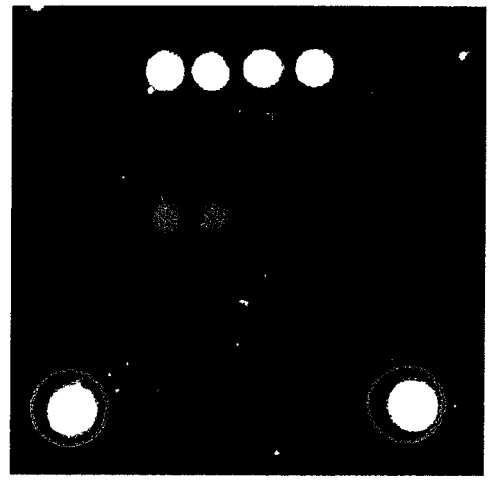
FIG. 3 shows an image obtained by measuring fluorescence after a hybridization reaction was performed in a microarray.
Figure 4:
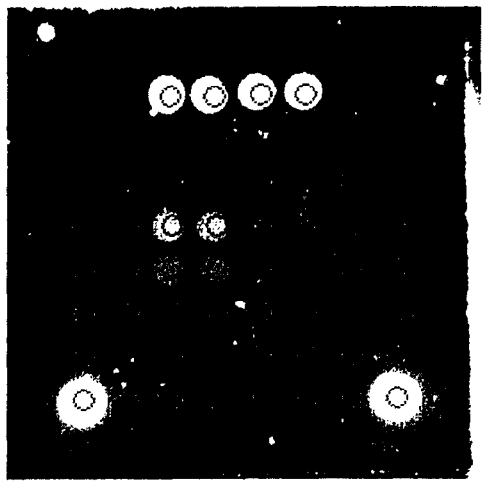
FIG. 4 shows the coordinates of each detection spot indicated by red circles, which were obtained by calculating and arranging them based on the coordinates of reference spots at two positions.

FIG. 3 shows an image obtained by measuring fluorescence after hybridization. FIG. 4 shows the coordinates of each detection spot indicated by red circles, which were obtained by calculation and arrangement based on the coordinates of reference spots at two positions. The mean fluorescence intensity of spots was 59473. It was demonstrated that simultaneous hybridization of the PCR product and the fluorescence-labeled oligo DNA did not affect each other.

Figure 5:
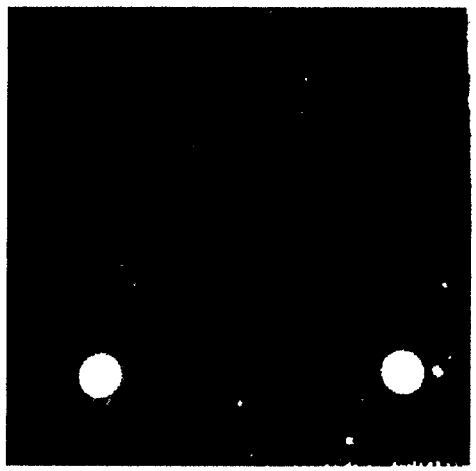
FIG. 5 shows a fluorescence image obtained by hybridizing only fluorescence-labeled oligo DNA without addition of any PCR product (in case of the specimen was faulty).

FIG. 5 shows a fluorescence image obtained by hybridization in (3) of only fluorescence-labeled oligo DNA alone without addition of any PCR product. Sufficient fluorescence intensity was obtained only at the reference spots. Also, non-specific fluorescence was not observed at the other spots. Based on the results, it was considered that fluorescence-labeled oligo DNA does not affect the detection results.

Figure 6:
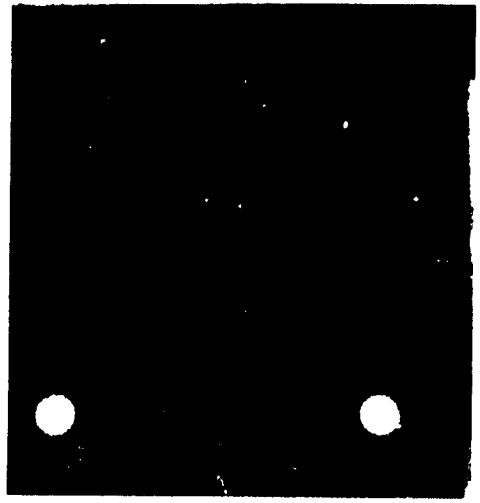
FIG. 6 shows a fluorescence image obtained by performing PCR amplification without template DNA, mixing 2 µl of the reaction solution with 1 µl of a hybridization buffer supplemented with fluorescence-labeled oligo DNA and then performing hybridization (in case of the specimen was faulty).

FIG. 6 shows a fluorescence image obtained by performing PCR amplification in (1) without addition of template DNA (lambda phage genomic DNA), mixing 2 μL of the reaction solution with 1 μL of a hybridization buffer supplemented with fluorescence-labeled oligo DNA, and performing hybridization. Fluorescence was observed only at reference spots and no fluorescence was observed at detection spots.

Figure 7:
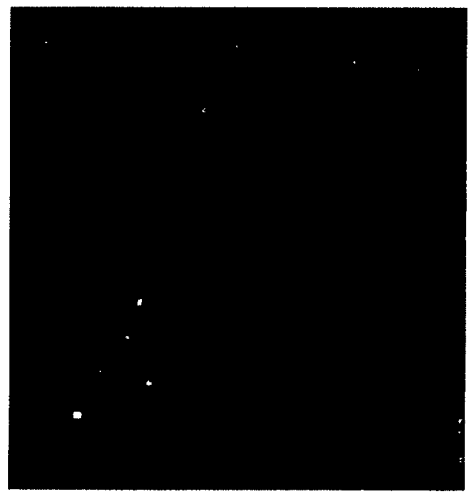
FIG. 7 shows a fluorescence image obtained by performing hybridization using ultrapure water instead of a hybridization buffer (in case of the hybridization was faulty).

FIG. 7 shows a fluorescence image obtained by performing hybridization in (2) using ultrapure water instead of a hybridization buffer (3×SSC/0.3% SDS)). No fluorescence was observed at any spots including, reference spots. It was thus revealed that fluorescence is not observed at reference spots unless hybridization is performed under appropriate conditions and thus hybridization failure can be detected based on the presence or the absence of fluorescence at reference spots.

When FIG. 6 was compared with FIG. 7, no fluorescence was observed at detection spots, as is apparent in both figures, but in FIG. 6, fluorescence was observed only at reference spots. In an actual test, if no fluorescence is observed at detection spots, it is generally difficult to determine if the result is due to the presence of defective specimens and/or PCR amplification failure or hybridization failure. However, according to the method of the present invention, when fluorescence is observed only at reference spots, it can at least be determined that the quality of the microarray and hybridization are sufficient. In this manner, possible defects in specimens or PCR failure can be inferred.

Industrial Applicability

According to the present invention, reliability of each microarray can be determined and thus measurement can be performed using a reliable microarray. Furthermore, reliability of a hybridization reaction can also be determined. Therefore, erroneous determination or erroneous detection can be avoided. Also, through combination with an automatic reactor and the like, measurement with a microarray can be automatically performed with high reliability.

All publications, patents, and patent applications cited herein are incorporated herein by reference in their entirety.

The invention claimed is:

1. A method for detecting hybridization between a probe polynucleotide and a target polynucleotide using a microarray, comprising the steps of:
   1) bringing a fluorescence-labeled target polynucleotide and a fluorescence-labeled marker polynucleotide capable of hybridizing to a reference polynucleotide into contact with a microarray having reference spots at one or more positions at which the reference polynucleotide is immobilized, and a plurality of detection spots at which the probe polynucleotide is immobilized;
   2) washing the microarray to remove unreacted marker and target polynucleotides;
   3) measuring fluorescence at the reference spots and determining that the measured value meets a predetermined level; and
   4) measuring fluorescence at each detection spot;
wherein, in the microarray, the detection spots and the reference spots are aligned, the reference spots are present at two or more positions, and the position of a detection spot is determined based on the distance of the detection spot from the reference spots and the angles between a line connecting each detection spot and a reference spot and the reference line, wherein the reference line is a line connecting two reference spots.

2. The method according to claim 1, wherein the fluorescent label of the marker polynucleotide is identical to that of the target polynucleotide.

3. The method according to claim 1, wherein the detection spots and the reference spots are arranged in a lattice pattern so that the circumference thereof is quadrangular and the reference spots are present at different vertices of the quadrangle.

4. The method according to claim 1, further comprising determining the position of a detection spot, wherein in the microarray, the detection spots and the reference spots are aligned and arranged in a square or rectangular lattice pattern and the reference spots are present at two positions located at vertices of the lattice.

5. The method according to claim 1, wherein the marker polynucleotide has 95% or more homology with a polynucleotide complementary to the reference polynucleotide.

* * * * *

```
                        SEQUENCE LISTING

<160> NUMBER OF SEQ ID NOS: 5

<210> SEQ ID NO 1
<211> LENGTH: 22
<212> TYPE: DNA
<213> ORGANISM: Artificial
<220> FEATURE:
<223> OTHER INFORMATION: Synthetic DNA

<400> SEQUENCE: 1
actggccgtc gttttacaac gt                                           22

<210> SEQ ID NO 2
<211> LENGTH: 22
<212> TYPE: DNA
<213> ORGANISM: Artificial
<220> FEATURE:
<223> OTHER INFORMATION: Synthetic DNA

<400> SEQUENCE: 2
ttgtccgcgc cgggcttcgc tc                                           22

<210> SEQ ID NO 3
<211> LENGTH: 20
<212> TYPE: DNA
<213> ORGANISM: Artificial
<220> FEATURE:
<223> OTHER INFORMATION: Synthetic DNA

<400> SEQUENCE: 3
acagggaatg cccgttctgc                                              20
```

```
<210> SEQ ID NO 4
<211> LENGTH: 20
<212> TYPE: DNA
<213> ORGANISM: Artificial
<220> FEATURE:
<223> OTHER INFORMATION: Synthetic DNA

<400> SEQUENCE: 4
aataaccgac acgggcagac                                                   20

<210> SEQ ID NO 5
<211> LENGTH: 22
<212> TYPE: DNA
<213> ORGANISM: Artificial
<220> FEATURE:
<223> OTHER INFORMATION: Synthetic DNA

<400> SEQUENCE: 5
acgttgtaaa acgacggcca gt                                                22
```